United States Patent
Alla et al.

(10) Patent No.: US 9,376,407 B2
(45) Date of Patent: Jun. 28, 2016

(54) PROCESS FOR PREPARATION OF LINEZOLID AND ITS NOVEL INTERMEDIATES

(75) Inventors: Raghu Mitra Alla, Hyderabad (IN); Ajay Kumar Dubey, Hyderabad (IN); Aruna Kumari Sirigiri, Hyderabad (IN); Naga Kama Kumar Mareedu, Hyderabad (IN)

(73) Assignee: Lee Pharma Limited, Moosapet, Balanagar, Hyderabad (IN)

( * ) Notice: Subject to any disclaimer, the term of this patent is extended or adjusted under 35 U.S.C. 154(b) by 0 days.

(21) Appl. No.: 13/820,568

(22) PCT Filed: Feb. 21, 2012

(86) PCT No.: PCT/IN2012/000121
§ 371 (c)(1),
(2), (4) Date: Mar. 4, 2013

(87) PCT Pub. No.: WO2012/114355
PCT Pub. Date: Aug. 30, 2012

(65) Prior Publication Data
US 2013/0324719 A1    Dec. 5, 2013

(30) Foreign Application Priority Data
Feb. 24, 2011 (IN) .......................... 2451/CHE/2010

(51) Int. Cl.
C07D 263/06   (2006.01)
C07D 263/20   (2006.01)
C07D 263/14   (2006.01)
C07D 265/30   (2006.01)
C07D 269/00   (2006.01)
C07D 413/10   (2006.01)
A61K 31/5377   (2006.01)

(52) U.S. Cl.
CPC .......... *C07D 263/06* (2013.01); *A61K 31/5377* (2013.01); *C07D 263/20* (2013.01); *C07D 263/14* (2013.01); *C07D 265/30* (2013.01); *C07D 269/00* (2013.01); *C07D 413/10* (2013.01)

(58) Field of Classification Search
CPC .. C07D 211/60; C07D 401/04; C07D 211/58; C07D 211/62; C07D 211/16
USPC .................................................. 544/106, 137
See application file for complete search history.

(56) References Cited

U.S. PATENT DOCUMENTS 5,688,792 A * 11/1997 Barbachyn et al. ........ 514/235.5
5,837,870 A    11/1998 Pearlman et al.
2007/0032472 A1   2/2007 Mohan Rao et al.

FOREIGN PATENT DOCUMENTS

EP    1737850 B1 †  3/2007
EP    1737850 B1 * 10/2007
WO    WO 2011/137222 A1   11/2011

OTHER PUBLICATIONS

Reddy, K., S. M. Rao, G. O. Reddy, T. Suresh, J. M. Babu, P. K. Dubey, K. Vyas. "Isolation and characterization of process-related impurities in linezolid." Journal of Pharmaceutical and Biomedical Assays 30 (2002): pp. 635-642.*
S. Roehrig et. al.: " Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59/7939): An Oral, Direct Factor Xa Inhibitor ,"Journal of Medicinal Chemistry, vol. 48, No. 19, Aug. 18, 2009, pp. 5900-5908.
International Search report issued in corresponding application PCT/IN2012/000121, dated Oct. 8, 2012.
Krishna Reddy, et al., Isolation and characterization of process-related impurities in linezolid.†
Communication pursuant to Article 94(3) EPC, Application No. 12 716 665.0-1462, Date Apr. 25, 2014, Applicant Lee Pharma Limited.†
Third Party Observation for application No. EP20120716665, Applicant: Lee Pharma Ltd, Publication No. EP2595968.†
V Suresh Reddy, Application No. EP20120716665, Novel Process for Preparation of Linezolid and Its Novel Intermediates, Lee Pharma, Ltd, date of filing Feb. 21, 2012.†
Communicaiton Application No. 12 716 665.0-1462, Lee Pharma Limited dated Apr. 25, 2014.†
Krishna Reddy, et al., Isolation and characterization of process-related impurities in linezolid, Journal of Pharmaceutical and Biomedical Analysis 30 2002, 635-642.†

* cited by examiner
† cited by third party

*Primary Examiner* — Alicia L Otton
*Assistant Examiner* — Sagar Patel
(74) *Attorney, Agent, or Firm* — Davidson, Davidson & Kappel LLC

(57) ABSTRACT

A novel process for preparing oxazolidinone antibacterial agent Linezolid including key intermediates of oxazolidinones comprising: reacting 3-fluoro-4-morpholinyl aniline with R-epichlorohydrin; carbonylation to form oxazolidinone derivative; acetylation of (5R)-5-(chloromethyl)-3-(3-fluoro-4-morpholinophenyl-oxazolidin-2-one with sodium acetate to get novel intermediate; hydrolysis of (R)-3-(3-fluoro-4-morpholinophenyl)-2-oxo-5-oxazolidinyl methyl acetate; mesylation of (R)-3-(3-fluoro-4-morpholinophenyl)-2-oxo-5-oxazolidinyl methanol; reaction of (R)-3-(3-fluoro-4-morpholinophenyl)-2-oxo-5-oxazolidinyl methyl methane sulphonate with potassium phthalimide; hydrolysis of (S)-3-(3-fluoro-4-morpholinophenyl)-2-oxo-5-oxazolidinyl methyl phthalimide with hydrazine hydrate; acetylation of (S)-3-(3-fluoro-4-morpholinophenyl)-2-oxo-5-oxazolidinyl methyl amine with acetic anhydride yields Linezolid in high yield.

15 Claims, No Drawings

PROCESS FOR PREPARATION OF LINEZOLID AND ITS NOVEL INTERMEDIATES

This application is a U.S. national phase application of International Application No. PCT/IN2012/000121, filed on Feb. 21, 2012, which claims priority to Indian Patent Application No. 2451/CHE/2010, filed Feb. 24, 2011, the disclosures of which are all hereby incorporated by reference herein.

FIELD OF INVENTION

The present invention relates to a novel process for the preparation of oxazolidinone antibacterial agent Linezolid and their key intermediates.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, anaerobic organisms such as bacteroides and clostridia species & acid-fast organisms such as mycobacterium tuberculosis & mycobacterium avium.

Among lower antibacterial agents, Linezolid is a recent synthetic class of antimicrobial active against a number of pathogenic microorganisms. Linezolid [(S)—N-[[3-[3-fluoro-4-(4-morpholinyl)phenyl]-2-oxo-5-oxazolidinyl]methyl]acetamide] is disclosed in U.S. Pat. No. 5,688,792. It is marketed in US by Pfizer Inc having the brand name Zyvox®.

We have discovered and developed a novel intermediate and novel process, which is useful to prepare Linezolid. The process has the potential to lower the cost of commercial production of Linezolid. We also discovered novel key intermediates, which are more useful in the currently known process.

It has been found that U.S. Pat. No. 5,688,792 described the process for the preparation of Linezolid as described in scheme.

Scheme-1:

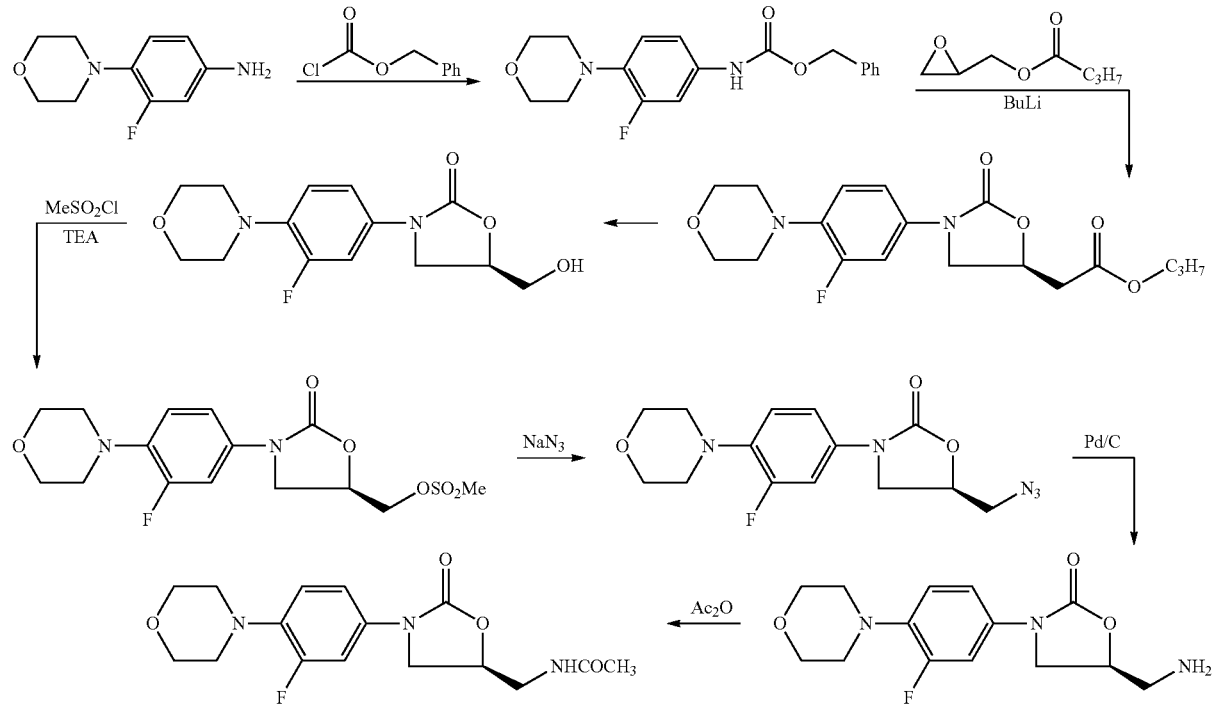

Further is U.S. 2007/0032472 A1 discloses two processes for the preparation of Linezolid in a different route as described in the following scheme.

Scheme-2:

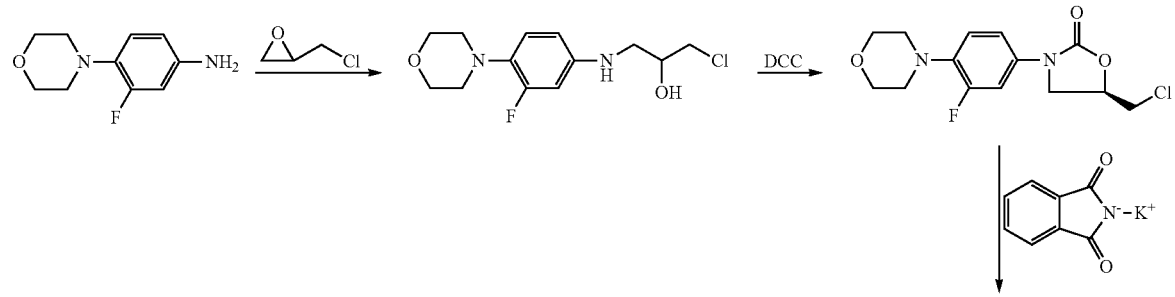

-continued

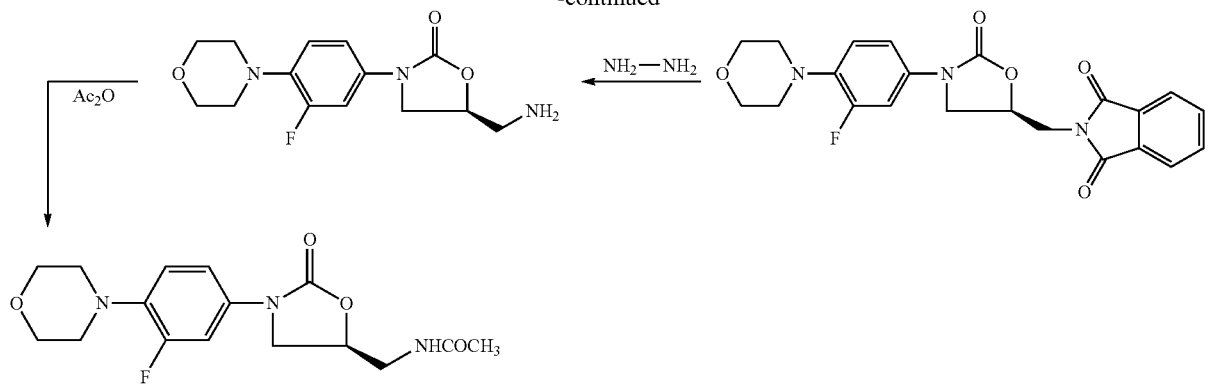

The above mentioned base patent describes the preparation of hydroxy derivative by using hazardous chemical like n-BuLi at the temperature of −78° C. with reported very low yield. This process is not commercially viable and very difficult to handle BuLi as well as the very lower temperature.

In other mentioned patent process other unwanted isomer as well as unspecified impurities forms more, which are very difficult to remove and these impurities are continue to be present in the final drug Linezolid, and during the removal process yield becomes very low.

This has prompted and necessitated further research in an attempt to develop a novel route to avoid the formation of the impurity and to maximize the yield. We have discovered and developed a novel process for the preparation of novel intermediates, which are useful for the preparation of antimicrobial Linezolid. Another objective of the present invention is to provide improved method for the preparation of Linezolid avoiding the drawbacks of the hitherto known process. This process has the potential to significantly lower the cost of commercial production of Linezolid.

OBJECT OF THE INVENTION

Primary object of the invention is to provide a novel process for preparation of oxazolidinone antibacterial agent Linezolid.

Another object of the invention is to provide a novel process for preparation of key intermediates for preparing Linezolid.

SUMMARY OF THE INVENTION

The present invention provides a process to prepare Linezolid

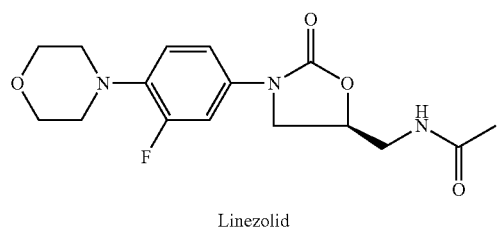 [SMILES: CC(=O)NC[C@H]1CN(c2ccc(N3CCOCC3)c(F)c2)C(=O)O1]

Linezolid

Which comprises;

Step (a): Reacting [3-fluoro-4-morpholinyl aniline] of formula IX with R-epichlorohydrin

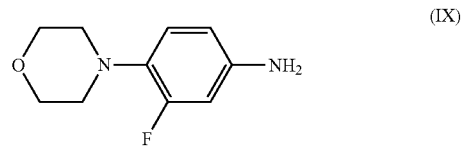 [SMILES: Nc1ccc(N2CCOCC2)c(F)c1]
(IX)

Step (b): Carbonylation of Compound Structure VIII

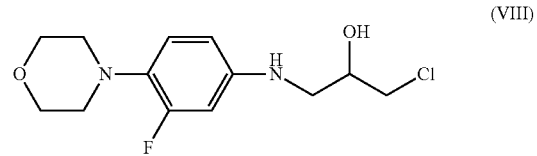 [SMILES: OC(CCl)CNc1ccc(N2CCOCC2)c(F)c1]
(VIII)

Step (C): Acetylation of Compound Structure VII

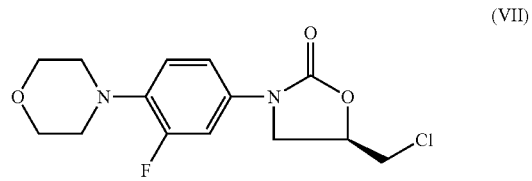 [SMILES: O=C1O[C@@H](CCl)CN1c1ccc(N2CCOCC2)c(F)c1]
(VII)

Step (d): Hydrolysis of Compound Structure (VI)

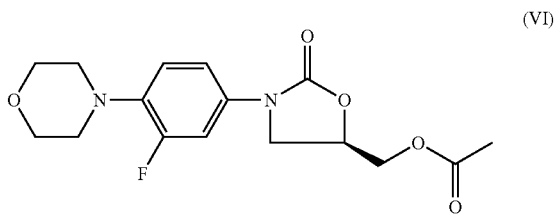 [SMILES: CC(=O)OC[C@H]1CN(c2ccc(N3CCOCC3)c(F)c2)C(=O)O1]
(VI)

Step (e): Mesylation of Compound Structure (V)
Step (g): Deprotection of Compound Structure (III)
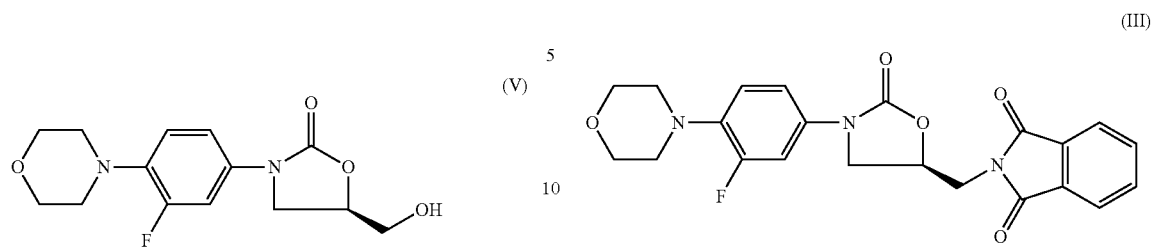
Step (f): Imidation of Compound Structure (IV)
Step (h): Acetylation of Compound Structure (II)
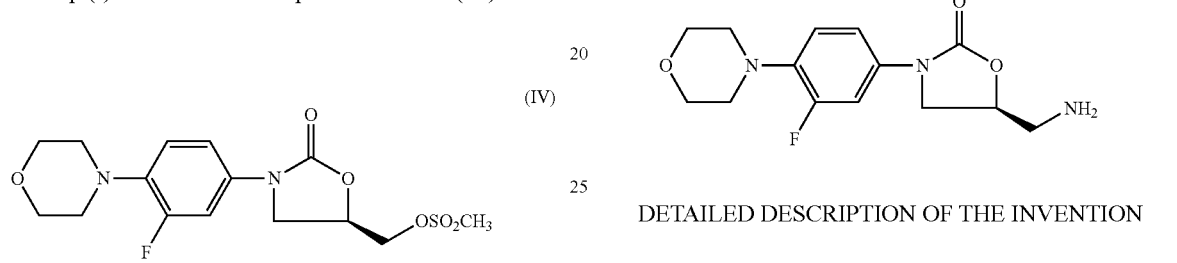
DETAILED DESCRIPTION OF THE INVENTION
The process of the present invention is illustrated in scheme-3:
Scheme-3:
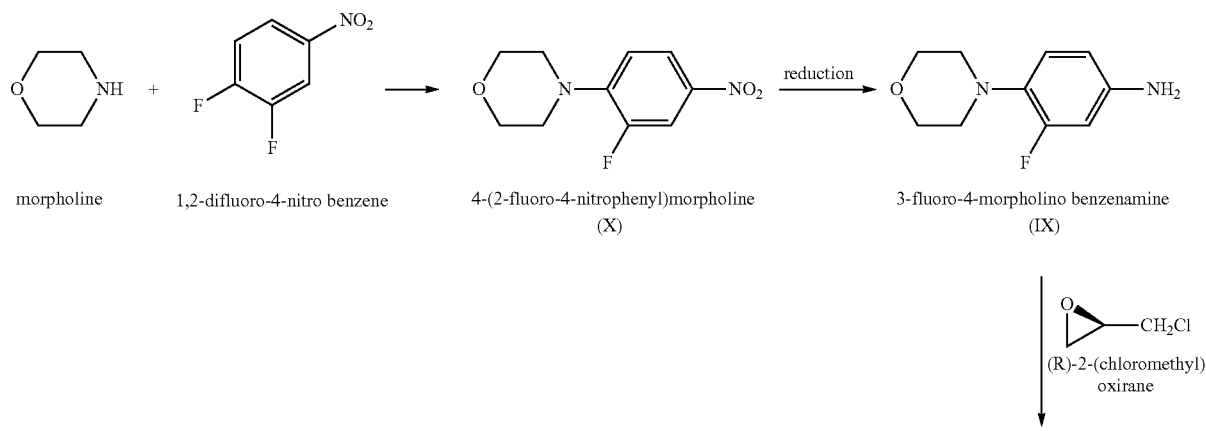
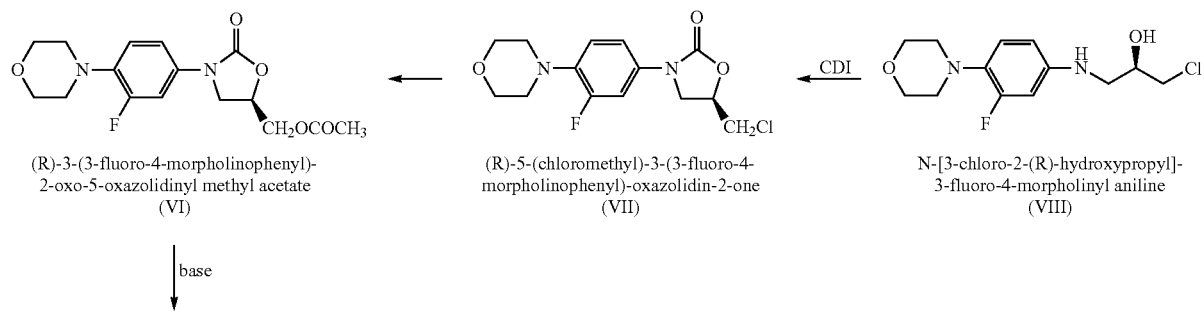

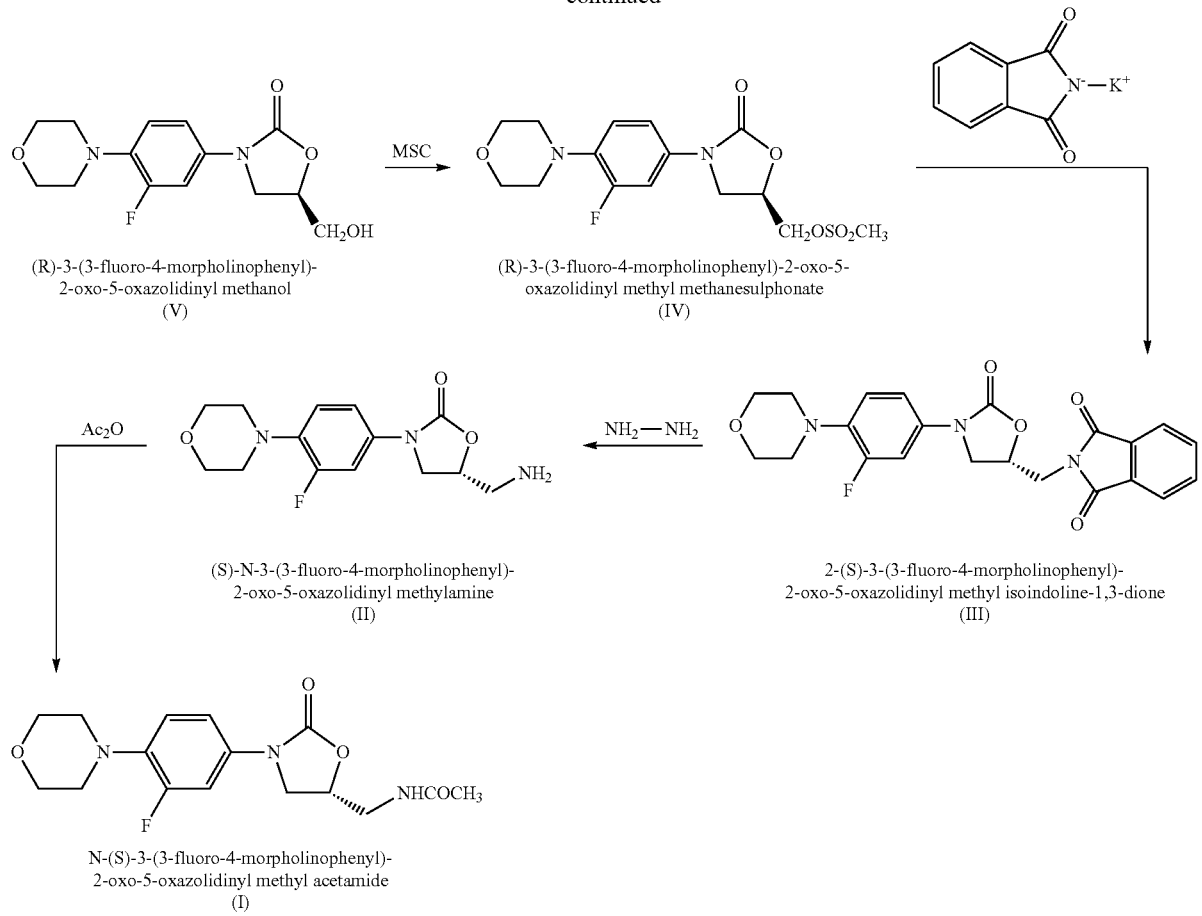

The present invention provides a process for the preparation of novel intermediate of the formula useful for the preparation of Linezolid of formula (I), which comprises:

(i) Reacting the compound 1,2-difluoro-4-nitrobenzene with morpholine in presence of an organic base and solvent at a temperature in the range of 70-80° C. to form the known intermediate of the formula X.

The base such as triethylamine, diisopropylamine, and pyridine, most preferably triethylamine may be used in step (i). Condensation can be carried out by known methods such as those described in U.S. Pat. No. 5,688,792.

(ii) Reduction of the compound of the formula X in presence of catalyst and solvent at a temperature in the range of 25-60° C. to form a known intermediate of the formula IX.

The catalyst such as Hydrose, palladium, Raney Nickel, Zinc can be used. Preferably, palladium/Carbon, most preferably Raney Nickel may be used in step (ii). The solvents used may be selected from methanol, water, isopropyl alcohol, ethanol, and ethylacetate. Most preferably, methanol can be used as a solvent. There reaction temperature may preferably between 25-60° C. and most preferably between 40-45° C. Raney Nickel can be used 10-30%, preferably 20% catalyst, most preferably 15% catalyst can be used. The hydrogen gas pressure can apply in the range of 4.0-6.0 kg/cm$^2$; most preferably 4.0-4.5 kg/cm$^{-2}$ can be applied.

(iii) Reaction of compound of formula IX with R-epichlorohydrin in presence of alcohol to produce known intermediate of formula VIII.

The solvent such as DMF, DMAc, acetonitrile, sec. butanol, IPA, tert. butanol. Most preferably tert. butanol is used. The quantity of epichlorohydrin is a critical, but for better yield and highest enantiomeric purity. 1.25 molar equivalents are used with respect to 3-fluoro-4-morpholinyl aniline and for reaction completion purpose. The reaction is carried out at boiling temperature for about 16 hrs is required for reaction completion.

(iv) The Carbonylation reaction of compound of formula VIII with dicarbonylimidazolyl by known methods to produce intermediate of formula VII.

The solvent is selected for isolation/crystallization of formula VII from n-butyl acetate, sec. butyl acetate, ethyl acetate, and methyl acetate. Preferably solvent can be ethyl acetate, most preferably solvent can be n-butyl acetate to produce better quality of this intermediate.

(v) The acetylation reaction of compound of formula VII in presence of aprotic solvent to form novel intermediate of formula VI.

The acetylating agents such as sodium acetate (anhydrous), Sodium acetate (mono hydrate), sodium acetate (trihydrate) & potassium acetate can be used. Most preferably, sodium acetate anhydrous can be used in the molar equivalents of 1.0-2.5 equivalents. Most preferably, sodium acetate anhydrous 2.0 molar equivalents can be used.

The solvent selected from aprotic solvents such as dimethyl formamide, dimethyl sulphoxide, and dimethyl acetamide, most preferably dimethyl formamide. The reaction temperature may preferably between 90-130° C. and most (vi) Hydrolysis reaction of compound formula VI in presence of non-polar solvents and in presence of base to produce novel compound of formula V.

Non-polar solvent is selected from tetrahydrofuran, toluene, hexane, most preferable solvent can be tetrahydrofuran. The basic hydrolysis inorganic base is selected from NaOH, $Na_2CO_3$, $NaHCO_3$, sodium tert. butoxide, potassium tert. butoxide. Most preferably sodium tert. butoxide can be used in the 1.0-1.5 molar equivalents. The reaction temperature may preferably between 0-15° C., most preferably 10-15° C.

(vii) Mesylation reaction of compound of formula V with methane sulphonyl chloride in presence of methylene dichloride can be carried out by known methods as described in U.S. Pat. No. 5,688,792.

(viii) Reaction of compound of formula IV with potassium phthalimide in presence of dimethyl formamide to produce known intermediate of formula III by known methods.

The reaction temperature is between 80-140° C. and most preferably the reaction temperature is 120° C.

(ix) Reaction of compound of formula III with hydrazine hydrate or aqueous methylamine to produce compound of formula II. These methods of deprotection are known and described in U.S. Pat. No. 5,688,792.

(x) (S)—N-3-(3-fluoro-4-morpholinophenyl)-2-oxo-5-oxazolidinyl methylamine is reacted with acetic anhydride to produce compound of formula I (Linezolid).

The present invention is more particularly described and explained in the following examples.)

EXAMPLES (S)—N-3-(3-fluoro-4-morpholinophenyl)-2-oxo-5-oxazolidinyl methyl acetamide Step (1): 3-fluoro-4-morpholinyl nitrobenzene 3,4-difluoro nitrobenzene (100 gr) is slowly added to a mixture of morpholine (76.6 gr), triethylamine (23 ml) and in presence of acetonitrile solvent (115 ml) at 40-50° C. Reaction mass is heated for 6 hrs at reflux temperature, cooled to 25-30° C. Then water (600 ml) is added slowly to the reaction mass and then cooled to 0-5° C. The reaction mixture is stirred for 1 hr. The solid is filtered to give 134 gr of 3-fluoro-4-morpholinyl nitrobenzene.

Step (2): 3-fluoro-4-morpholinyl aniline

Methanol (1.35 Lt) and 3-fluoro-4-morpholinyl nitrobenzene (134 gr) are added into autoclave and followed by Raney Nickel (20.5 gr). The system was flushed with nitrogen and hydrogen gas. The pressure of hydrogen was set to 4.0 kg/cm$^-$2. The reaction mixture was stirred at 45-50° C. under $H_2$ pressure for 8 hrs & the reaction followed by TLC until completion. The reaction mixture was filtered through celite and the filtrate is distilled off evaporate solvent completely U/vacuum at <50° C. temperature. Reaction mass is cooled to 25-30° C. To this DM water (400 ml) is added, Stirred for 1 hr at 25-30° C. The solid is filtered to give 105 gr of 3-fluoro-4-morpholinyl aniline.

Step (3): N-[3-chloro-2-(R)-hydroxy propyl]-3-fluoro-4-morpholinyl aniline 3-fluoro-4-morpholinyl aniline (100 gr) is mixed with R-epichlorohydrin (59 gr) tert-butanol (500 ml) is added and heated for 16 hrs at reflux temperature. The solvent is distilled to give 156 gr of N-[3-chloro-2-(R)-hydroxy propyl]-3-fluoro-4-morpholinyl aniline.

Step (4): (5R)-5-(chloromethyl)-3-(3-fluoro-4-morpholinophenyl)-oxazolidin-2-one N-[3-chloro-2-(R)-hydroxypropyl]-3-fluoro-4-morpholinyl aniline (156 gr) is dissolved in methylene dichloride (1.5 Lt), diimidazolyl carbonyl (87.4 gr) is added at room temperature, stirred for 24 hrs at 25-30° C. Then washed thrice with water (750 ml×3). Dry over $Na_2SO_4$. Distilled methylene dichloride to give 156 gr of crude (5R)-5-(chloromethyl)-3-[3-fluoro-4-[4-morpholinyl]phenyl]-2-oxazolidinone, which is further isolated and crystallized from n-butyl acetate (100 ml) to give 83 gr of (5R)-5-(chloromethyl)-3-(3-fluoro-4-morpholinophenyl)-oxazolidin-2-one.

Step (5): (R)-3-(3-fluoro-4-morpholinophenyl)-2-oxo-5-oxazolidinyl methyl acetate (5R)-5-(chloromethyl)-3-(3-fluoro-4-morpholinophenyl)-oxazolidin-2-one (83 gr) is mixed with sodium acetate (43 and dimethyl formamide (320 ml) is added. Reaction mass is heated to 120° C. and stirred for 8-10 hrs. It is then cooled to 25-30° C. Filter the inorganic salts and washed with DMF (10 ml). DM water (1.0 Lt) is added to round bottom flask. Slowly add above said reaction mass to water at 20-05° C. for a period of 60 min and stirred for 30 min at 20-25° C. Filtered the precipitated solid, dried the material for 5-6 hrs at 50° C. to give 65 gr of (R)-3-(3-fluoro-4-morpholinophenyl)-2-oxo-5-oxazolidinyl methyl acetate.

Step (6): (R)-3-(3-fluoro-4-morpholinophenyl)-2-oxo-5-oxazolidinyl methanol (R)-3-(3-fluoro-4-morpholinophenyl)-2-oxo-5-oxazolidinyl methyl acetate (62 gr) is mixed with tetrahydrofuran (300 ml), cooled to 0-5° C. Slowly added sodium tert-butoxide (17.5 gr) at 0-5° C. and followed by slow addition of DM water (620 ml) at 10-15° C. The reaction mass is stirred for 30 min at 10-15° C., After completion of the reaction, methylene dichloride is added (300 ml), further extracted with methylene dichloride (120 ml). Solvent is evaporated completely U/vacuum. The precipitated solid is crystallized from hexane (150 ml). Isolated solid is filtered and washed with hexane. Dried the material at 50-55° C. to give 50 gr of (R)-3-(3-fluoro-4-morpholinophenyl)-2-oxo-5-oxazolidinyl methanol.

Step (7): (R)-3-(3-fluoro-4-morpholinophenyl)-2-oxo-5-oxazolidinyl methyl methanesulphonate (R)-3-(3-fluoro-4-morpholinophenyl)-2-oxo-5-oxazolidinyl methanol (50 gr) and triethylamine (42.6 gr) in methylene dichloride (250 ml) was cooled in ice-bath and treated with methane sulphonyl chloride (38.2 gr). The mixture was stirred for 30 min at 0-5° C. The precipitated product is filtered and washed with chilled DM water (250 ml). Dried the material at 50-55° C. to give 40 gr of (R)-3-(3-fluoro-4-morpholinophenyl)-2-oxo-5-oxazolidinyl methyl methanesulphonate.

Step (8): (S)-3-(3-fluoro-4-morpholinophenyl)-2-oxo-5-oxazolidinyl methyl phthalimide The mixture of (R)-3-(3-fluoro-4-morpholinophenyl)-2-oxo-5-oxazolidinyl methyl methanesulphonate (30 gr), potassium phthalimide (19.4 gr) and dimethyl formamide (180 ml) is heated for 2 hrs at 120° C. temperature. The reaction mixture is cooled to 0-5° C., slowly added 360 ml of DM water and filtered the solid to give 27 gr of (S)-3-(3-fluoro-4-morpholinophenyl)-2-oxo-5-oxazolidinyl methyl phthalimide.

Step (9): (S)-3-(3-fluoro-4-morpholinophenyl)-2-oxo-5-oxazolidinyl methyl amine

Methanol (150 ml) and hydrazine hydrate (16.2 gr) are added to flask containing (S)-3-(3-fluoro-4-morpholinophenyl)-2-oxo-5-oxazolidinyl methyl phthalimide (25 gr), heated for 1 hr at reflux temperature and cooled to room temperature. Distill off solvent completely U/vaccum at 45° C. Then water (125 ml) is added to the reaction mass and extracted with methylene dichloride (62 ml×2). The combined extractions were washed with water (62 ml) and the solvent is distilled to give 15 gr of (S)-3-(3-fluoro-4-morpholinophenyl)-2-oxo-5-oxazolidinyl methylamine.

Step (10): (S)-3-(3-fluoro-4-morpholinophenyl)-2-oxo-5-oxazolidinyl methyl acetamide (S)-3-(3-fluoro-4-morpholinophenyl)-2-oxo-5-oxazolidinyl methylamine (15 gr) is dissolved in ethylacetate (150 ml); acetic anhydride (15 gr) is added dropwise at ambient temperature and stirred for 1 hr. The reaction mixture is then cooled to 0-5° C. Filtered the solid to give 12 gr of (S)-3-(3-fluoro-4-morpholinophenyl)-2-oxo-5-oxazolidinyl methyl acetamide.

We claim:

1. A process for preparation of (R)-3-(3-fluoro-4-morpholinophenyl)-2-oxo-5-oxazolidinyl methanol of formula V

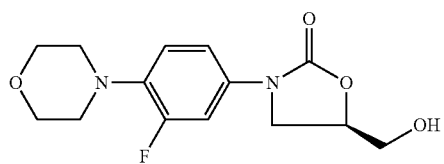

which comprises:

a) reacting a compound of formula IX

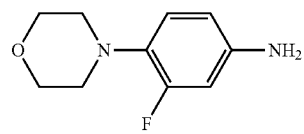

with R-epichlorohydrin to produce a compound of formula VIII

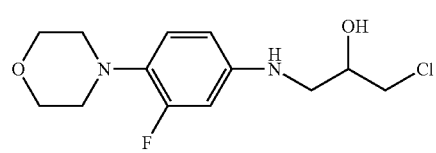

which is further converted to chloromethyl oxazolidinone compound of formula VII and is crystallized

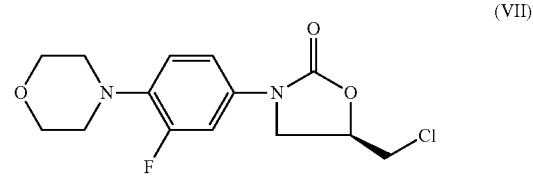 [SMILES: O=C1O[C@@H](CCl)CN1c1ccc(N2CCOCC2)c(F)c1]

b) reacting the compound of formula VII with sodium acetate to produce a compound of formula VI

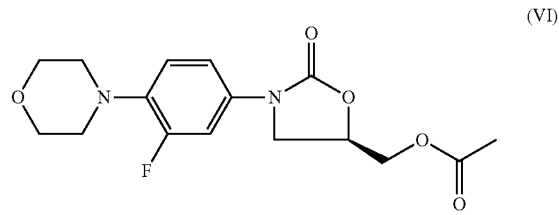 [SMILES: CC(=O)OC[C@H]1CN(c2ccc(N3CCOCC3)c(F)c2)C(=O)O1]

c) hydrolysis of the product of step (b) to hydroxy methyl oxazolidinone compound of formula V

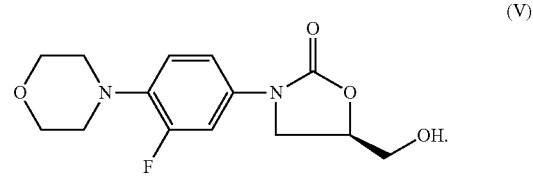 [SMILES: O=C1O[C@@H](CO)CN1c1ccc(N2CCOCC2)c(F)c1]

2. The process according to claim 1, wherein chloromethyl oxazolidinone is crystallized from an organic solvent.

3. The process according to claim 2, wherein the solvent is selected from ethylacetate and n-butyl acetate.

4. The process according to claim 3, wherein the solvent is n-butyl acetate.

5. The process according to claim 1, wherein the chloromethyl oxazolidinone compound of formula VII is converted in step (b) to the acetyl derivative of the compound of formula VI as defined in claim 1, which comprises reacting the said chloromethyl oxazolidinone with anhydrous sodium acetate in a reaction solvent to give the acetyl compound of formula VI

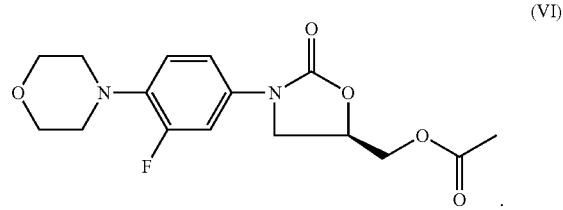 [SMILES: CC(=O)OC[C@H]1CN(c2ccc(N3CCOCC3)c(F)c2)C(=O)O1]

6. The process according to claim 5, wherein the quantity of sodium acetate is at least 2.0 molar equivalents to compound of formula VII.

7. The process according to claim 5, wherein the reaction solvent is selected from aprotic solvent.

8. The process according to claim 7, wherein the reaction solvent is DMF.

9. The process according to claim 5, wherein the reaction is carried out at a temperature of 120° C.

10. The process according to claim 1, wherein acetyl oxazolidinone compound of formula VI is hydrolyzed in the step (c) to a hydroxy derivative of the compound of formula V as defined in claim 1, which comprises reacting the said acetyl oxazolidinone with a base in the presence of a solvent or a mixture of solvents to give the hydroxy compound of formula V

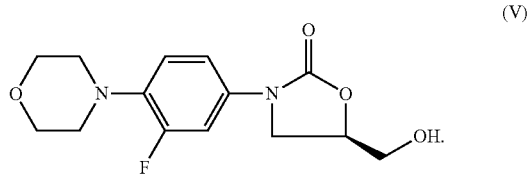

(V)

11. The process according to claim 10, wherein the base is sodium tert-butoxide.

12. The process according to claim 10, wherein the reaction solvent is THF or a mixture of THF and water.

13. The process according to claim 11, wherein the quantity of sodium tert. butoxide is at least one molar equivalent to the compound of formula VI.

14. The process according to claim 10, wherein the reaction temperature is about 10-15° C.

15. A process for the preparation of Linezolid of formula

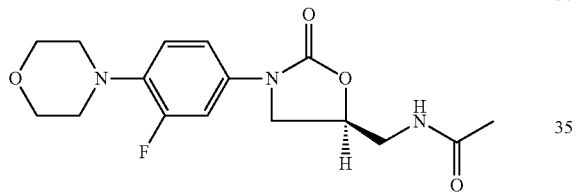

which comprises:

(a) reaction of 3-fluoro-4-morpholinyl aniline with R-epichlorohydrin to give N-[3-chloro-2-(R)-hydroxypropyl]-3-fluoro-4-morpholinyl aniline;

(b) carbonylation of N-[3-chloro-2-(R)-hydroxypropyl]-3-fluoro-4-morpholinyl aniline to produce (5R)-5-(chloromethyl)-3-(3-fluoro-4-morpholinophenyl)-oxazolidin-2-one;

(c) acetylation of (5R)-5-(chloromethyl)-3-(3-fluoro-4-morpholinophenyl)-oxazolidin-2-one with sodium acetate to produce (R)-3-(3-fluoro-4-morpholinophenyl)-2-oxo-5-oxazolidinyl methyl acetate;

d) hydrolysis of (R)-3-(3-fluoro-4-morpholinophenyl)-2-oxo-5-oxazolidinyl methyl acetate with sodium tert.-butoxide to provide (R)-3-(3-fluoro-4-morpholinophenyl)-2-oxo-5-oxazolidinyl methanol;

e) mesylation of (R)-3-(3-fluoro-4-morpholinophenyl)-2-oxo-5-oxazolidinyl methanol to provide (R)-3-(3-fluoro-4-morpholinophenyl)-2-oxo-5-oxazolidinyl methyl methanesulphonate;

f) reaction of (R)-3-(3-fluoro-4-morpholinophenyl)-2-oxo-5-oxazolidinyl methyl methanesulphonate with potassium phthalimide to give (S)-3-(3-fluoro-4-morpholinophenyl)-2-oxo-5-oxazolidinyl methyl phthalimide;

g) deprotection of (S)-3-(3-fluoro-4-morpholinophenyl)-2-oxo-5-oxazolidinyl methyl phthalimide with hydrazine hydrate to provide (S)-3-(3-fluoro-4-morpholinophenyl)-2-oxo-5-oxazolidinyl methyl amine;

h) acetylation of (S)-3-(3-fluoro-4-morpholinophenyl)-2-oxo-5-oxazolidinyl methylamine with acetic anhydride to give Linezolid in high yield and high enantiomeric purity.

* * * * *